United States Patent [19]

Murdock

[11] Patent Number: 4,540,788

[45] Date of Patent: Sep. 10, 1985

[54] SCHIFF BASES OF [(AMINOALKYL OR SUBSTITUTED AMINOALKYL)AMINO]-9,10-ANTHRA-CENEDIONES

[75] Inventor: Keith C. Murdock, Pearl River, N.Y.

[73] Assignee: American Cyanamid Company, Stamford, Conn.

[21] Appl. No.: 513,577

[22] Filed: Jul. 14, 1983

[51] Int. Cl.³ .................................. C07D 401/10
[52] U.S. Cl. ...................................... 546/264; 549/59; 549/472; 260/378; 260/380; 514/332; 514/444; 514/461; 514/647
[58] Field of Search .................. 546/264; 549/59, 472; 260/378, 380; 424/263, 285, 275, 330

[56] References Cited

U.S. PATENT DOCUMENTS 4,197,249 4/1980 Murdock et al. .................. 260/380
4,258,181 3/1981 Murdock et al. ............ 260/239 BC

OTHER PUBLICATIONS

Venditti Pharmacological Basis of Cancer Chemotherapy 1975, pp. 245-270.
Silverstein, The Science, 8/7/81, pp. 19-22.

Primary Examiner—Jane T. Fan
Attorney, Agent, or Firm—Edward A. Conroy, Jr.

[57] ABSTRACT

This disclosure describes novel Schiff bases of 1,4-bis[(ω-aminoalkyl)amino]-9,10-anthracenediones and leuco bases thereof which are useful as chelating agents and for inducing regression of leukemia and/or inhibiting tumor growth in mammals.

16 Claims, No Drawings

SCHIFF BASES OF [(AMINOALKYL OR SUBSTITUTED AMINOALKYL)AMINO]-9,10-ANTHRACENEDIONES

BRIEF SUMMARY OF THE INVENTION

This invention relates to new organic compounds and, more particularly, is concerned with novel symmetrical Schiff bases of 1,4-bis[($\omega$-aminoalkyl)amino]-9,10-anthracenediones which may be represented by the following structural formula:

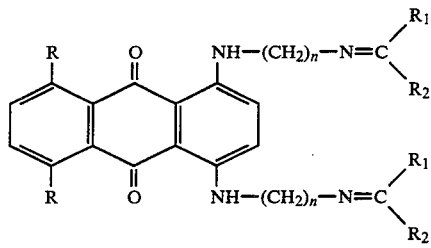

(I, aromatic bases)

wherein n is 2 or 3; R is hydrogen or hydroxy; $R_1$ is hydrogen or alkyl having from one to three carbon atoms; $R_2$ is hydrogen, alkyl having from one to six carbon atoms, 1-naphthyl, 2-naphthyl, 2-furyl, 3-furyl, 2-thienyl, 3-thienyl, 2-pyridyl, 3-pyridyl, 4-pyridyl, pentafluorophenyl or a moiety of the formula:

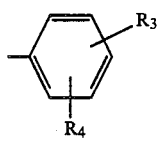

wherein $R_3$ and $R_4$ are each independently selected from the group consisting of hydrogen, hydroxy, fluoro, chloro, bromo, cyano, trifluoromethyl, alkyl having from one to three carbon atoms, alkoxy having from one to three carbon atoms, dimethylamino and benzyloxy; and $R_1$ and $R_2$ taken together is —$(CH_2)_m$— wherein m is 4,5 or 6.

A preferred embodiment of the present invention may be represented by the following structural formula:

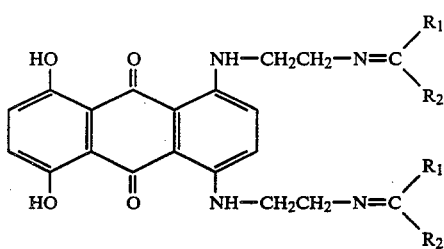

wherein $R_1$ and $R_2$ are as hereinabove defined.

Also included within the purview of the present invention are the leuco bases and tautomers thereof which may be represented by the following formulae:

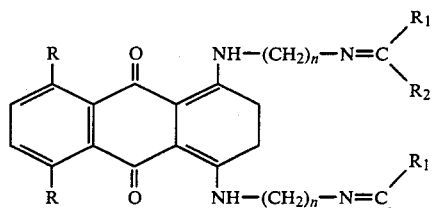

(II, leuco bases)

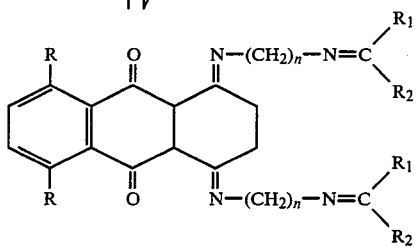

(III, tautomeric form)

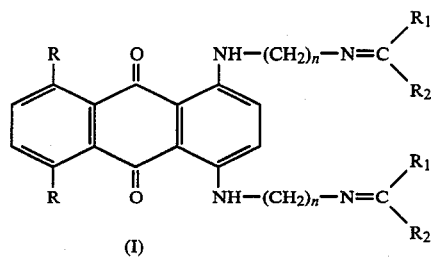

(I)

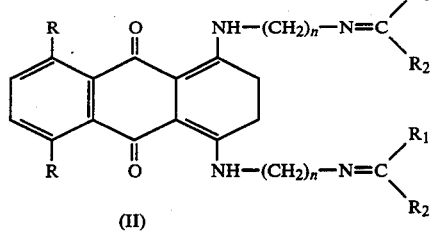

(II)

wherein n, R, $R_1$ and $R_2$ are as hereinbefore defined. In accordance with the above reaction scheme, leuco 1,4,5,8-tetrahydroxy-9,10-anthracenedione or leuco 1,4-dihydroxy-9,10-anthracenedione (IV) is condensed with an excess of an appropriate alhylene diamine (V) such as ethylenediamine or 1,3-propanediamine in a solvent such as N,N,N',dimethylformamide, or mixtures thereof at from about 30° C. to about 70° C. under an atmosphere of nitrogen for several hours to produce the corresponding leuco bases (VI). The leuco bases (VI) may be readily oxidized to the fully aromatic derivatives (VII) by a variety of methods such as air oxidation or treatment with chloranil, hydrogen peroxide or sodium perborate.

A suspension of the aromatic derivative (VII)

DETAILED DESCRIPTION OF THE INVENTION

The novel compounds of the present invention are obtainable as blue, dark blue or blue-black solids having characteristic melting points and absorption spectra.

The novel compounds of the present invention may be readily prepared in accordance with the following reaction scheme:

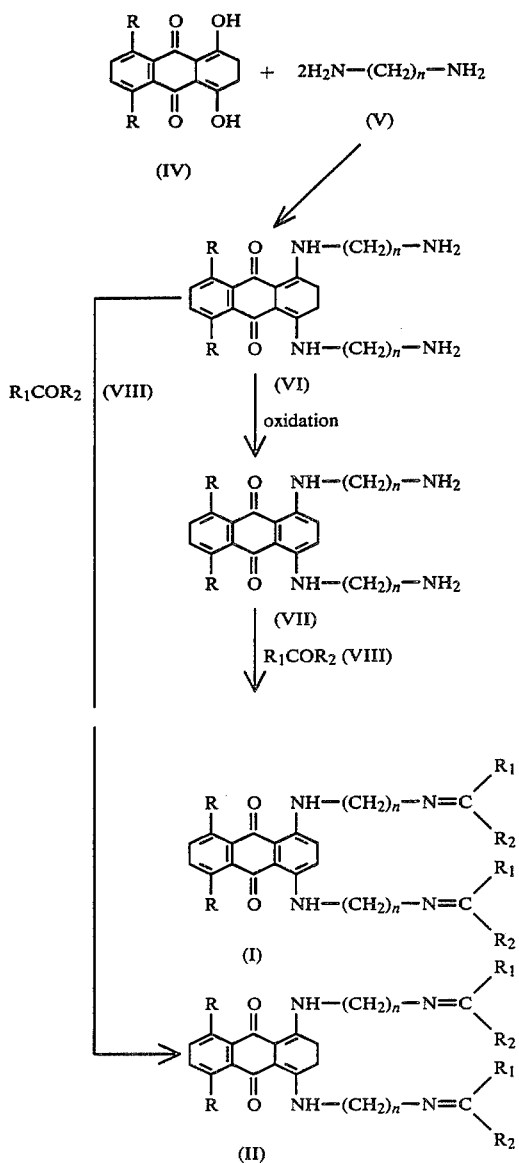

wherein n, R, $R_1$ and $R_2$ are as hereinabefore defined. In accordance with the above reaction scheme, leuco 1,4,5,8-tetrahydroxy-9,10-anthracenedione or leuco 1,4-dihydroxy-9,10-anthracenedione (IV) is condensed with an excess of an appropriate alkylene diamine (V) such as ethylenediamine or 1,3-propanediamine in a solvent such as N,N,N',N'-tetramethylethylenediamine, methanol, ethanol, water, dimethylformamide, or mixtures thereof at from about 30° C. to about 70° C. under an atmosphere of nitrogen for several hours to produce the corresponding leuco bases (VI). The leuco bases (VI) may be readily oxidized to the fully aromatic derivatives (VII) by a variety of methods such as air oxidation or treatment with chloranil, hydrogen peroxide or sodium perborate.

A suspension of the aromatic derivative (VII) or the leuco base (VI) in benzene or toluene containing an aldehyde or ketone (VIII) is stirred and heated at the reflux temperature for 2–8 hours using a Dean-Stark trap or molecular sieves to remove by-product water from the distillate. Undissolved solid is removed by filtration of the hot solution. The filtrate is allowed to stand at room temperature for 2–30 days with slow evaporation to crystallize the desired product I or II. The solid is collected by filtration and washed with a minimal amount of ether.

The novel compounds described herein are useful as chelating, complexing or sequestering agents. The complexes formed with polyvalent metal ions are particularly stable. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds.

Certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), Deran, Greenberg, MacDonald, Schumacher and Abbott. These protocols have established standardized screening tests which are generally followed in the field of testing for antitumoral agents. Two of these systems are particularly significant to the present invention. They are lymphocyctic leukemia P388 and melanotic melanoma B16. These neoplasms are found in mice. Generally, good antitumor activity, shown in these protocols by a percentage increase of mean survival times of the treated (T) animals over the control (C) animals, is predictive of similar results in human leukemias. A mean survival time ratio $T/C \times 100 \geq 125\%$ is considered necessary to demonstrate antineoplastic activity by the substance being tested.

The novel compounds of the present invention possess the property of inhibiting the growth of transplanted mouse tumors as established by the following tests.

Lymphocytic Leukemia P388 Test

The animals used were $BDF_1$ mice all of one sex, weighing a minimum of 17 g. and all within a 3 g. weight range. There were 5 or 6 animals per test group. The tumor transplant was by intraperitoneal injection of 0.5 ml. of dilute ascitic fluid containing $10^6$ cells of lymphocytic leukemia P388. The test compounds were administered intraperitoneally on days one, 5 and 9 (relative to tumor inoculation) at various doses. The animals were weighed and survivors recorded on a regular basis for 30 days. The median survival time and the ratio of survival time for treated (T)/control (C) animals were calculated. The positive control compound was 1,4-dihydroxy-5,8-bis[[2-(2-hydroxyethylamino)ethyl]amino]-9,10-anthracenedione dihydrochloride, (U.S. Pat. No. 4,197,249; claim 19) given as a 0.025, 0.1, 0.4 or 1.6 mg/kg injection, or the bis(2-imidazolin-2-ylhydrazone) of 9,10-anthracenedicarboxaldehyde dihydrochloride (U.S. Pat. No. 4,258,181; claim 2) given as a 0.1, 0.4, 1.6 or 6.4 mg/kg injection or 5-fluorouracil given as a 60 mg/kg injection. The results of this test with representative compounds of the present invention appear in Table I. The criterion for efficacy is T/C×100≧125%.

TABLE I

Lymphocytic Leukemia P388 Test

| Compound | Dose mg/kg | Median Survival Time (Days) | T/C × 100 (Percent) |
|---|---|---|---|
| 1,4-Dihydroxy-5,8-bis[[2-[(pentafluorophenyl)methylene]amino]ethyl]-9,10-anthracenedione (1st test) | 50 | >28 | >250 |
| | 12 | 23 | 205 |
| | 3 | 19.5 | 174 |
| Control | | 11.2 | |
| 1,4-Dihydroxy-5,8-bis[[2-(2-hydroxyethylamino)ethyl]amino]-9,10-anthracenedione dihydrochloride | 0.4 | 23.5 | 210 |
| 1,4-Dihydroxy-5,8-bis[[2-[(pentafluorophenyl)methylene]amino]ethyl]-9,10-anthracenedione (2nd test) | 50 | 22 | 220 |
| | 12 | 17 | 170 |
| | 3 | 20 | 200 |
| | 0.8 | 19 | 190 |
| | 0.2 | 16.5 | 165 |
| Control | | 10.0 | |
| 1,4-Dihydroxy-5,8-bis[[2-(2-hydroxyethylamino)ethyl]amino]-9,10-anthracenedione dihydrochloride | 0.1 | 25.5 | 255 |
| 1,4-Dihydroxy-5,8-bis[[2-[(phenylmethylene)amino]ethyl]amino]-9,10-anthracenedione (1st test) | 25 | 22 | 210 |
| | 6 | >30 | >286 |
| | 1.5 | 28.5 | 271 |
| | 0.4 | 25 | 238 |
| Control | | 10.5 | |
| 1,4-Dihydroxy-5,8-bis[[2-(2-hydroxyethylamino)ethyl]amino]-9,10-anthracenedione dihydrochloride | 0.1 | 21.5 | 205 |
| 1,4-Dihydroxy-5,8-bis[[2-[(phenylmethylene)amino]ethyl]amino]-9,10-anthracenedione (2nd test) | 1.6 | >30 | >256 |
| | 0.4 | 21.5 | 184 |
| | 0.1 | 21 | 179 |
| | 0.025 | 19 | 162 |
| Control | | 11.7 | |
| 1,4-Dihydroxy-5,8-bis[[2-(2-hydroxyethylamino)ethyl]amino]-9,10-anthracenedione dihydrochloride | 0.1 | 21.5 | 184 |
| 1,4-Dihydroxy-5,8-bis[[2-[(1-naphthalenylmethylene)amino]ethyl]amino]-9,10-anthracenedione (1st test) | 6 | 28.5 | >271 |
| | 1.5 | 23 | 219 |
| | 0.4 | 18.5 | 176 |
| Control | | 10.5 | |
| 1,4-Dihydroxy-5,8-bis[[2-(2-hydroxyethylamino)ethyl]amino]-9,10-anthracenedione dihydrochloride | 0.1 | 21.5 | 205 |
| 1,4-Dihydroxy-5,8-bis[[2-[(1-naphthalenylmethylene)amino]ethyl]amino]-9,10-anthracenedione (2nd test) | 1.6 | 27.5 | 235 |
| | 0.4 | 24 | 205 |
| | 0.1 | 17 | 145 |
| | 0.025 | 16.5 | 141 |
| Control | | 11.7 | |
| 1,4-Dihydroxy-5,8-bis[[2-(2-hydroxyethylamino)ethyl]amino]-9,10-anthracenedione dihydrochloride | 0.1 | 21.5 | 184 |
| 1,4-Bis[[2-[[(2,4-dimethoxyphenyl)methylene]amino]ethyl]amino]-5,8-dihydroxy-9,10-anthracenedione (1st test) | 3 | 24 | 207 |
| Control | | 11.6 | |
| 1,4-Dihydroxy-5,8-bis[[2-(2-hydroxyethylamino)ethyl]amino]-9,10-anthracenedione dihydrochloride | 0.1 | 21.5 | 185 |
| 1,4-Bis[[2-[[(2,4-dimethoxyphenyl)methylene]amino]ethyl]amino]-5,8-dihydroxy-9,10-anthracenedione (2nd test) | 6.4 | 21.5 | 182 |
| | 1.6 | 21.5 | 182 |
| | 0.4 | 21 | 178 |
| | 0.1 | 15 | 127 |
| Control | | 11.8 | |
| 1,4-Dihydroxy-5,8-bis[[2-(2-hydroxyethylamino)ethyl]amino]-9,10-anthracenedione dihydrochloride | 0.1 | 19 | 154 |
| 1,4-Bis[[2-[(2-furanylmethylene)amino]ethyl]amino]-5,8-dihydroxy-9,10-anthracenedione (1st test) | 3 | 27 | 233 |
| Control | | 11.6 | |
| 1,4-Dihydroxy-5,8-bis[[2-(2-hydroxyethylamino)ethyl]amino]-9,10-anthracenedione dihydrochloride | 0.1 | 21.5 | 185 |

TABLE I-continued

Lymphocytic Leukemia P388 Test

| Compound | Dose mg/kg | Median Survival Time (Days) | T/C × 100 (Percent) |
|---|---|---|---|
| 1,4-Bis[[2-[(2-furanylmethylene)amino]ethyl]amino]-5,8-dihydroxy-9,10-anthracenedione (2nd test) | 6.4 | 21 | 178 |
| | 1.6 | 21 | 178 |
| | 0.4 | 18.5 | 157 |
| | 0.1 | 18 | 153 |
| Control | | 11.8 | |
| 1,4-Dihydroxy-5,8-bis[[2-(2-hydroxyethylamino)ethyl]amino]-9,10-anthracenedione dihydrochloride | 0.1 | 19 | 154 |
| 1,4-Bis[[2-[[(4-fluorophenyl)methylene]amino]ethyl]amino]-5,8-dihydroxy-9,10-anthracenedione (1st test) | 6 | 16 | 133 |
| | 1.5 | 28.5 | 238 |
| | 0.4 | 22 | 183 |
| Control | | 12.0 | |
| Bis(2-imidazolin-2-ylhydrazone)-9,10-anthracenedicarboxaldehyde dihydrochoride | 0.4 | 24.5 | 204 |
| 1,4-Bis[[2-[[(4-fluorophenyl)methylene]amino]ethyl]amino]-5,8-dihydroxy-9,10-anthracenedione (2nd test) | 1.6 | 21.5 | 182 |
| | 0.4 | 22 | 186 |
| | 0.1 | 17.5 | 148 |
| Control | | 11.8 | |
| 1,4-Dihydroxy-5,8-bis[[2-(2-hydroxyethylamino)ethyl]amino]-9,10-anthracenedione dihydrochloride | 0.1 | 21.5 | 182 |
| 1,4-Dihydroxy-5,8-bis[[2-[(3-pyridinylmethylene)amino]ethyl]amino]-9,10-anthracenedione (1st test) | 1.5 | 24 | 200 |
| | 0.4 | 20 | 167 |
| Control | | 12.0 | |
| Bis(2-imidazolin-2-ylhydrazone)-9,10-anthracenedicarboxaldehyde dihydrochloride | 0.4 | 24.5 | 204 |
| 1,4-Dihydroxy-5,8-bis[[2-[(3-pyridinylmethylene)amino]ethyl]amino]-9,10-anthracenedione (2nd test) | 1.6 | 25.5 | 216 |
| | 0.4 | 23.5 | 199 |
| | 0.1 | 17.5 | 148 |
| | 0.025 | 16.5 | 140 |
| Control | | 11.8 | |
| 1,4-Dihydroxy-5,8-bis[[2-(2-hydroxyethylamino)ethyl]amino]-9,10-anthracenedione dihydrochloride | 0.1 | 21.5 | 182 |
| 1,4-Dihydroxy-5,8-bis[[2-[[(3-methylphenyl)methylene)amino]ethyl]amino]-9,10-anthracenedione (1st test) | 6 | 15 | 125 |
| | 1.5 | 20.5 | 171 |
| | 0.4 | 15 | 125 |
| Control | | 12.0 | |
| Bis(2-imidazolin-2-ylhydrazone)-9,10-anthracenedicarboxaldehyde dihydrochloride | 0.4 | 24.5 | 204 |
| 1,4-Dihydroxy-5,8-bis[[2-[[(3-methylphenyl)methylene)amino]ethyl]amino]-9,10-anthracenedione (2nd test) | 1.6 | 23 | 195 |
| | 0.4 | 22 | 186 |
| | 0.1 | 20 | 169 |
| | 0.025 | 16.5 | 140 |
| Control | | 11.8 | |
| 1,4-Dihydroxy-5,8-bis[[2-(2-hydroxyethylamino)ethyl]amino]-9,10-anthracenedione dihydrochloride | 0.1 | 21.5 | 182 |
| 1,4-Dihydroxy-5,8-bis[[2-[[[4-(benzyloxy)phenyl]methylene]amino]ethyl]amino]-9,10-anthracenedione (1st test) | 25 | 15.5 | 129 |
| | 6 | >28 | >233 |
| | 1.5 | 23.5 | 196 |
| | 0.4 | 18.5 | 154 |
| Control | | 12.0 | |
| Bis(2-imidazolin-2-ylhydrazone)-9,10-anthracenedicarboxaldehyde dihydrochloride | 0.4 | 24.5 | 204 |
| 1,4-Dihydroxy-5,8-bis[[2-[[[4-(benzyloxy)phenyl]methylene]amino]ethyl]amino]-9,10-anthracenedione (2nd test) | 1.6 | 20.5 | 174 |
| | 0.4 | 16.5 | 140 |
| Control | | 11.8 | |
| 1,4-Dihydroxy-5,8-bis[[2-(2-hydroxyethylamino)ethyl]amino]-9,10-anthracenedione dihydrochloride | 0.1 | 21.5 | 182 |
| 1,4-Bis[[2-[[[4-(dimethylamino)phenyl]methylene]amino]ethyl]amino]-5,8-dihydroxy-9,10-antra- | 6 | 21 | 175 |
| | 1.5 | 21 | 175 |
| | 0.4 | 25.5 | 213 |

TABLE I-continued

Lymphocytic Leukemia P388 Test

| Compound | Dose mg/kg | Median Survival Time (Days) | T/C × 100 (Percent) |
|---|---|---|---|
| cenedione (1st test) | | | |
| Control | | 12.0 | |
| Bis(2-imidazolin-2-ylhydrazone)-9,10-anthracenedicarboxaldehyde dihydrochloride | 0.4 | 24.5 | 204 |
| 1,4-Bis[[2-[[[4-(dimethylamino)-phenyl]methylene]amino]ethyl]-amino]-5,8-dihydroxy-9,10-anthracenedione (2nd test) | 1.6 | 19.5 | 165 |
| | 0.4 | 20.5 | 174 |
| | 0.1 | 16.5 | 140 |
| Control | | 11.8 | |
| 1,4-Dihydroxy-5,8-bis[[2-(2-hydroxyethylamino)ethyl]amino]-9,10-anthracenedione dihydrochloride | 0.1 | 21.5 | 182 |
| 1,4-Dihydroxy-5,8-bis[[2-[(2-pyridinylmethylene)amino]ethyl]-amino]-9,10-anthracenedione | 6.25 | 28 | 280 |
| | 3.12 | >30 | >300 |
| | 1.56 | 22 | 220 |
| | 0.78 | 22 | 220 |
| Control | | 10.0 | |
| 5-Fluorouracil | 60 | 23.5 | 235 |
| 4,4'[(9,10-Dihydro-5,8-dihydroxy-9,10-dioxo-1,4-anthracenediyl)bis-(imino-2,1-ethanediylnitrilo-methylidyne)]bisbenzonitrile | 25 | 27.5 | 275 |
| | 12.5 | 25 | 250 |
| | 6.25 | 24 | 240 |
| | 3.12 | 21.5 | 215 |
| | 1.56 | 19.5 | 195 |
| | 0.78 | 22 | 220 |
| Control | | 10.0 | |
| 5-Fluorouracil | 60 | 23.5 | 235 |
| 1,4-Bis[[2-[[(3,5-dimethoxyphenyl)-methylene]amino]ethyl]amino]-5,8-dihydroxy-9,10-anthracenedione | 25 | 26 | 260 |
| | 12.5 | 21 | 210 |
| | 6.25 | 23 | 230 |
| | 3.12 | 23 | 230 |
| | 1.56 | 19.5 | 195 |
| | 0.78 | 17 | 170 |
| Control | | 10.0 | |
| 5-Fluorouracil | 60 | 23.5 | 235 |
| 1,4-Bis[[2-[[(2-bromophenyl)methyl-ene]amino]ethyl]amino]-5,8-dihy-droxy-9,10-anthracenedione | 25.0 | >30 | >300 |
| | 12.5 | 24.5 | 245 |
| | 6.25 | 20.5 | 205 |
| | 3.12 | 19 | 190 |
| | 1.56 | 19 | 190 |
| | 0.78 | 17 | 170 |
| Control | | 10.0 | |
| 5-Fluorouracil | 60 | 23.5 | 235 |
| 1,4-Dihydroxy-5,8-bis[[2-[[(2-hydroxy-4-methoxyphenyl)methylene]-amino]ethyl]amino]-9,10-anthra-cenedione | 25.0 | 26.5 | 265 |
| | 12.5 | 19.5 | 195 |
| | 6.25 | 25 | 250 |
| | 3.12 | 28.5 | 285 |
| | 1.56 | 24 | 240 |
| | 0.78 | 21 | 210 |
| Control | | 10.0 | |
| 5-Fluorouracil | 60 | 23.5 | 235 |
| 1,4-Dihydroxy-5,8-bis[[2-[(2-thienylmethylene)amino]ethyl]-amino]-9,10-anthracenedione | 25.0 | >30 | >300 |
| | 12.5 | 23 | 230 |
| | 6.25 | 19 | 190 |
| | 3.12 | 22.5 | 225 |
| | 1.56 | 20.5 | 205 |
| | 0.78 | 20.5 | 205 |
| Control | | 10.0 | |
| 5-Fluorouracil | 60 | 23.5 | 235 |
| 1,4-Dihydroxy-5,8-bis[[2-[[[3-(trifluoromethyl)phenyl]methylene]-amino]ethyl]amino]-9,10-anthra-cenedione | 25.0 | 24.5 | 245 |
| | 12.5 | 27 | 270 |
| | 6.25 | 20 | 200 |
| | 3.12 | 21 | 210 |
| | 1.56 | 20 | 200 |
| | 0.78 | 19 | 190 |
| Control | | 10.0 | |
| 5-Fluorouracil | 60 | 23.5 | 235 |
| 1,4-Dihydroxy-5,8-bis[[2-[[(4-methoxyphenyl)methylene]amino]-ethyl]amino]-9,10-anthracenedione | 25.0 | 28 | 280 |
| | 12.5 | 20.5 | 205 |
| | 6.25 | 25 | 250 |
| | 3.12 | 20 | 200 |
| | 1.56 | 19 | 190 |
| | 0.78 | 19.5 | 195 |
| Control | | 10.0 | |
| 5-Fluorouracil | 60 | 23.5 | 235 |

Melanotic Melanoma B16

The animals used are BDF$_1$ mice, all of the same sex, weighing a minimum of 17 g. and all within a 3 g. weight range. There are normally 6 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 or days one, five and nine (relative to tumor inoculation) at various doses. The animals are weighed and survivors are recorded on a regular basis for 60 days. The median survival time and the ratio of survival time for treated (T)/control (C) animals are calculated. The positive control compound used when the test compounds were administered on days one through nine was 1,4-dihydroxy-5,8-bis[[2-(2-hydroxyethylamino)ethyl]amino]-9,10-anthracenedione dihydrochloride, (U.S. Pat. No. 4,197,249; claim 19) given as a 0.025, 0.1, 0.4 or 1.6 mg/kg injection. When the test compounds were administered on days one, five and nine the positive control compound used was cyclophosphamide given as a 60 mg/kg injection. The results of this test with representative compounds of the present invention appear in Table II. The criterion for efficacy is T/C×100≧125%.

TABLE II

Melanotic Melanoma B16

| Compound | Dose mg/kg | Median Survival Time (Days) | T/C × 100 (Percent) |
|---|---|---|---|
| 1,4-Dihydroxy-5,8-bis[[2-[(penta-fluorophenyl)methylene]amino]-ethyl]-9,10-anthracenedione (1st test) | 25 | 38 | 205 |
| | 6 | >55 | >289 |
| | 1.5 | >60 | >316 |
| Control | | 18.8 | |
| 1,4-Dihydroxy-5,8-bis[[2-(2-hydroxyethylamino)ethyl]amino]-9,10-anthracenedione dihydrochloride | 0.1 | 31.5 | 166 |
| 1,4-Dihydroxy-5,8-bis[[2-[(penta-fluorophenyl)methylene]amino]-ethyl]-9,10-anthracenedione (2nd test) | 1.5 | >60 | >282 |
| | 0.4 | 48 | 225 |
| | 0.1 | 34 | 160 |
| | 0.025 | 27 | 127 |
| Control | | 21.3 | |
| 1,4-Dihydroxy-5,8-bis[[2-(2-hydroxyethylamino)ethyl]amino]-9,10-anthracenedione dihydrochloride | 0.025 | 33 | 155 |
| 1,4-Dihydroxy-5,8-bis[[2-[(phenyl-methylene)amino]ethyl]amino]-9,10-anthracenedione (1st test) | 1.6 | >60 | >288 |
| | 0.4 | 57 | 274 |
| | 1.0 | 52 | 250 |
| | 0.025 | 43.5 | 209 |
| Control | | 20.8 | |
| 1,4-Dihydroxy-5,8-bis[[2-(2-hydroxyethylamino)ethyl]amino]-9,10-anthracenedione dihydrochloride | 0.1 | 47 | 226 |
| 1,4-Dihydroxy-5,8-bis[[2-[(phenyl-methylene)amino]ethyl]amino]-9,10-anthracenedione (2nd test) | 0.2 | >60 | >235 |
| | 0.05 | 43.5 | 171 |
| | 0.0125 | 36 | 141 |
| Control | | 25.5 | |
| 1,4-Dihydroxy-5,8-bis[[2-(2-hydroxyethylamino)ethyl]amino]-9,10-anthracenedione dihydrochloride | 0.1 | 41.5 | 163 |
| 1,4-Dihydroxy-5,8-bis[[2-[(1-naphthalenylmethylene)amino]ethyl]amino]-9,10-anthracenedione (1st test) | 1.6 | >60 | >288 |
| | 0.4 | 52.5 | 252 |
| | 0.1 | 40 | 192 |
| | 0.025 | 37.5 | 180 |
| Control | | 20.8 | |
| 1,4-Dihydroxy-5,8-bis[[2-(2-hydroxyethylamino)ethyl]amino]-9,10-anthracenedione dihydrochloride | 0.1 | 47 | 226 |
| 1,4-Dihydroxy-5,8-bis[[2-[(1-naphthalenylmethylene)amino]ethyl]amino]-9,10-anthracenedione | 0.4 | >60 | >235 |
| | 0.1 | 52.5 | 206 |
| | 0.025 | 44.5 | 175 |

TABLE II-continued

Melanotic Melanoma B16

| Compound | Dose mg/kg | Median Survival Time (Days) | T/C × 100 (Percent) |
|---|---|---|---|
| (2nd test) | 0.006 | 39 | 153 |
| Control |  | 25.5 |  |
| 1,4-Dihydroxy-5,8-bis[[2-(2-hydroxyethylamino)ethyl]amino]-9,10-anthracenedione dihydrochloride | 0.1 | 41.5 | 163 |
| 1,4-Bis[[2-[[(2,4-dimethoxyphenyl)methylene]amino]ethyl]amino-5,8-dihydroxy-9,10-anthracenedione (1st test) | 3.2 | 32 | 154 |
|  | 0.8 | >60 | >288 |
|  | 0.2 | >60 | >288 |
|  | 0.05 | 51.5 | 248 |
| Control |  | 20.8 |  |
| 1,4-Dihydroxy-5,8-bis[[2-(2-hydroxyethylamino)ethyl]amino]-9,10-anthracenedione dihydrochloride | 0.1 | 47 | 226 |
| 1,4-Bis[[2-[[(2,4-dimethoxyphenyl)methylene]amino]ethyl]amino]-5,8-dihydroxy-9,10-anthracenedione (2nd test) | 0.2 | >60 | >235 |
|  | 0.05 | 42.5 | 167 |
|  | 0.025 | 40 | 157 |
| Control |  | 25.5 |  |
| 1,4-Dihydroxy-5,8-bis[[2-(2-hydroxyethylamino)ethyl]amino]-9,10-anthracenedione dihydrochloride | 0.1 | 41.5 | 163 |
| 1,4-Bis[[2-furanylmethylene)amino]ethyl]amino]-5,8-dihydroxy-9,10-anthracenedione (1st test) | 3.2 | 26.5 | 127 |
|  | 0.8 | >60 | >288 |
|  | 0.2 | >60 | >288 |
|  | 0.05 | >60 | >288 |
| Control |  | 20.8 |  |
| 1,4-Dihydroxy-5,8-bis[[2-(2-hydroxyethylamino)ethyl]amino]-9,10-anthracenedione dihydrochloride | 0.1 | 47 | 226 |
| 1,4-Bis[[2-[(2-furanylmethylene)amino]ethyl]amino]-5,8-dihydroxy-9,10-anthracenedione (2nd test) | 0.2 | >60 | >235 |
|  | 0.05 | 47.5 | 186 |
| Control |  | 25.5 |  |
| 1,4-Dihydroxy-5,8-bis[[2-(2-hydroxyethylamino)ethyl]amino]-9,10-anthracenedione dihydrochloride | 0.1 | 41.5 | 163 |
| 1,4-Bis[[2-[[(4-fluorophenyl)methylene]amino]ethyl]amino]-5,8-dihydroxy-9,10-anthracenedione (1st test) | 3.2 | 38.5 | 182 |
|  | 0.8 | >47 | >223 |
|  | 0.2 | >60 | >284 |
|  | 0.05 | 36.5 | 173 |
| Control |  | 21.1 |  |
| 1,4-Dihydroxy-5,8-bis[[2-(2-hydroxyethylamino)ethyl]amino]-9,10-anthracenedione dihydrochloride | 0.1 |  |  |
| 1,4-Bis[[2-[[(4-fluorophenyl)methylene]amino]ethyl]amino]-5,8-dihydroxy-9,10-anthracenedione (2nd test) | 0.4 | >60 | >305 |
|  | 0.1 | 35 | 178 |
|  | 0.025 | 31.5 | 160 |
| Control |  | 19.7 |  |
| 1,4-Dihydroxy-5,8-bis[[2-(2-hydroxyethylamino)ethyl]amino]-9,10-anthracenedione dihydrochloride | 0.1 | >53.5 | >272 |
| 1,4-Dihydroxy-5,8-bis[[2-[(3-pyridinylmethylene)amino]ethyl]amino]-9,10-anthracenedione (1st test) | 3.2 | 29 | 137 |
|  | 0.8 | >60 | >284 |
|  | 0.2 | >52 | >246 |
|  | 0.05 | 48.5 | 230 |
| Control |  | 21.1 |  |
| 1,4-Dihydroxy-5,8-bis[[2-(2-hydroxyethylamino)ethyl]amino]-9,10-anthracenedione dihydrochloride | 0.1 | 39.5 | 187 |
| 1,4-Dihydroxy-5,8-bis[[2-[(3-pyridinylmethylene)amino]ethyl]amino]-9,10-anthracenedione (2nd test) | 0.4 | >48.5 | >246 |
|  | 0.1 | 33 | 168 |
|  | 0.025 | 29.5 | 150 |
|  | 0.006 | 25.5 | 129 |
| Control |  | 19.7 |  |
| 1,4-Dihydroxy-5,8-bis[[2-(2-hydroxyethylamino)ethyl]amino]-9,10-anthracenedione dihydrochloride | 0.1 | >53.5 | >272 |
| 1,4-Dihydroxy-5,8-bis[[2-[[(3-methylphenyl)methylene)amino]ethyl]amino]-9,10-anthracenedione (1st test) | 3.2 | 33 | 156 |
|  | 0.8 | 45 | 213 |
|  | 0.2 | 47 | 223 |
|  | 0.05 | 33.5 | 159 |
| Control |  | 21.1 |  |
| 1,4-Dihydroxy-5,8-bis[[2-(2-hydroxyethylamino)ethyl]amino]-9,10-anthracenedione dihydrochloride | 0.1 | 39.5 | 187 |
| 1,4-Dihydroxy-5,8-bis[[2-[[(3-methylphenyl)methylene]amino]ethyl]amino]-9,10-anthracenedione (2nd test) | 0.4 | >55 | >279 |
|  | 0.1 | 34.5 | 175 |
|  | 0.025 | 26.5 | 135 |
| Control |  | 19.7 |  |
| 1,4-Dihydroxy-5,8-bis[[2-(2-hydroxyethylamino)ethyl]amino]-9,10-anthracenedione dihydrochloride | 0.1 | >53.5 | >272 |
| 1,4-Dihydroxy-5,8-bis[[2-[[[4-(benzyloxy)phenyl]methylene]amino]ethyl]amino]-9,10-anthracenedione (1st test) | 3.2 | >60 | >284 |
|  | 0.8 | 48.5 | 230 |
|  | 0.2 | 47.5 | 225 |
|  | 0.05 | 36 | 171 |
| Control |  | 21.1 |  |
| 1,4-Dihydroxy-5,8-bis[[2-(2-hydroxyethylamino)ethyl]amino]-9,10-anthracenedione dihydrochloride | 0.1 | 39.5 | 187 |
| 1,4-Dihydroxy-5,8-bis[[2-[[[4-(benzyloxy)phenyl]methylene]amino]ethyl]amino]-9,10-anthracenedione (2nd test) | 0.4 | 47.5 | 241 |
|  | 0.1 | 35.5 | 180 |
|  | 0.025 | 25.5 | 129 |
| Control |  | 19.7 |  |
| 1,4-Dihydroxy-5,8-bis[[2-(2-hydroxyethylamino)ethyl]amino]-9,10-anthracenedione dihydrochloride | 0.1 | >53.5 | >272 |
| 1,4-Bis[[2-[[[4-(dimethylamino)phenyl]methylene]amino]ethyl]amino]-5,8-dihydroxy-9,10-anthracenedione (1st test) | 3.2 | >60 | >284 |
|  | 0.8 | >60 | >284 |
|  | 0.2 | 45.5 | 216 |
|  | 0.025 | 33 | 156 |
| Control |  | 21.1 |  |
| 1,4-Dihydroxy-5,8-bis[[2-(2-hydroxyethylamino)ethyl]amino]-9,10-anthracenedione dihydrochloride | 0.1 | 39.5 | 187 |
| 1,4-Bis[[2-[[[4-(dimethylamino)phyenyl]methylene]amino]ethyl]amino]-5,8-dihydroxy-9,10-anthracenedione (2nd test) | 0.4 | >52.5 | >266 |
|  | 0.1 | 37 | 188 |
| Control |  | 19.7 |  |
| 1,4-Dihydroxy-5,8-bis[[2-(2-hydroxyethylamino)ethyl]amino]-9,10 anthracenedione dihydrochloride | 0.1 | >53.5 | >272 |
| 1,4-Dihydroxy-5,8-bis[[2-[(2-pyridinylmethylene)amino]ethyl]amino]-9,10-anthracenedione | 3.12 | >60 | >300 |
|  | 0.78 | >60 | >300 |
|  | 0.19 | 38.5 | 193 |
| Control |  | 20.0 |  |
| Cyclophosphamide | 60 | 28 | 140 |
| 4,4'-[(9,10-Dihydro-5,8-dihydroxy-9,10-dioxo-1,4-anthracenediyl)bis-(imino-2,1-ethanediylnitrilomethylidyne)]bisbenzonitrile | 12.5 | >60 | >300 |
|  | 3.12 | 35.5 | 178 |
|  | 0.78 | 42 | 210 |
| Control |  | 20.0 |  |
| Cyclophosphamide | 60 | 28 | 140 |
| 1,4-Bis[[2-[[(3,5-dimethoxyphenyl)methylene]amino]ethyl]amino]-5,8-dihydroxy-9,10-anthracenedione | 12.5 | >60 | >300 |
|  | 3.12 | >60 | >300 |
|  | 0.78 | 41 | 205 |
| Control |  | 20.0 |  |
| Cyclophosphamide | 60 | 28 | 140 |
| 1,4-Bis[[2-[[(2-bromophenyl)methylene]amino]ethyl]amino]-5,8-dihydroxy-9,10-anthracenedione | 12.5 | >60 | >300 |
|  | 3.12 | 35.5 | 178 |
|  | 0.78 | 28 | 140 |
| Control |  | 20.0 |  |
| Cyclophosphamide | 60 | 28 | 140 |
| 1,4-Dihydroxy-5,8-bis[[2-[[(2-hydroxy-4-methoxyphenyl)methylene]amino]ethyl]amino]-9,10-anthracenedione | 50 | 43 | 239 |
|  | 12.5 | 40 | 222 |
|  | 3.12 | 35.5 | 197 |
|  | 0.78 | 23 | 128 |
| Control |  | 18.0 |  |
| Cyclophosphamide | 60 | 25.5 | 142 |
| 1,4-Dihydroxy-5,8-bis[[2-[(2-thienylmethylene)amino]ethyl]amino]-9,10-anthracenedione | 50 | 32.5 | 181 |
|  | 12.5 | >60 | >333 |
|  | 3.12 | 40.5 | 225 |
|  | 0.78 | 31 | 172 |
| Control |  | 18.0 |  |
| Cyclophosphamide | 60 | 25.5 | 142 |

TABLE II-continued

Melanotic Melanoma B16

| Compound | Dose mg/kg | Median Survival Time (Days) | T/C × 100 (Percent) |
| --- | --- | --- | --- |
| 1,4-Dihydroxy-5,8-bis[[2-[[[3-(trifluoromethyl)phenyl]methylene]-amino]ethyl]amino]-9,10-anthracenedione | 100 | 24 | 150 |
| | 50 | 47 | 294 |
| | 12.5 | 35.5 | 222 |
| | 3.12 | 27.5 | 172 |
| | 0.78 | 22 | 138 |
| Control | | 16.0 | |
| Cyclophosphamide | 60 | 25.5 | 159 |
| 1,4-Dihydroxy-5,8-bis[[2-[[(4-methoxyphenyl)methylene)amino]-ethyl]amino]-9,10-anthracenedione | 12.5 | 45.5 | 284 |
| | 3.12 | 43 | 269 |
| | 0.78 | 27.5 | 172 |
| Control | | 16.0 | |
| Cyclophosphamide | 60 | 25.5 | 159 |

Also embraced within the purview of the present invention are therapeutic compositions of matter useful for ameliorating cancer diseases in mammals which contain the novel Schiff bases of the present invention as the active ingredients thereof. This aspect of the invention includes the novel compositions of matter and the method of inducing the regression and/or palliation of leukemia and related cancers in mammals when administered in amounts ranging from about 0.075 mg. to about 300 mg. per square meter of body surface area per day. The interrelationship of dosages for animals of various sizes and species and humans (based on mg/m$^2$ of surface area) is described by Freireich, E. J., et al., Quantititive Comparison of Toxicity of Anticancer Agents in Mouse, Rat, Hamster, Dog, Monkey and Man, Cancer Chemother. Rep., 50, No. 4, 219–244, May 1966. A preferred dosage regimen for optimum results would be from about 3.0 mg/m$^2$/day to about 150 mg/m$^2$/day. Such dosage units are employed that a total of from about 0.5 mg. to about 525 mg. of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium contaning, for exmple, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin.

Sterile injectable solutions are prepared by incorporating the active compound in the required amount on the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg., with from about 10 to about 500 mg. being preferred. Expressed in proportions, the active compound is generally present in from about 0.1 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

1,4-Dihydroxy-5,8-bis[[2-[(pentafluorophenyl)methylene]amino]ethyl]-9,10-anthracenedione A 26.0 g amount of 1,4-bis[(2-aminoethyl)amino]-5,8-dihydroxyanthraquinone dihydrochloride (prepared as described in Example 23 of U.S. Pat. No. 4,197,249) was added to 800 ml of water and was mechanically stirred at room temperature for 16 hours. The resulting suspension was centrifuged for one hour. The supernatant solution was decanted and filtered through diatomaceous earth. The pellet was washed with water by centrifugation. The supernatant solutions were filtered through diatomaceous earth and combined, giving a total volume of 1500 ml.

A 450 ml amount of the above filtrate and 45 ml of concentrated ammonium hydroxide was stirred at room temperature as the originally flocculent solid became more granular. The solid was collected by filtration and washed with water, then dried in vacuo at 70° C. for 16 hours to yield 4.5 g of the free base 1,4-bis[(2-aminoethyl)amino]-5,8-dihydroxyanthraquinone as a blue black solid, mp 350° C.

A suspension of 1.46 g (0.0041 moles) of the preceding free base in 50 ml of benzene containing 2.40 g (0.0123 moles) of pentafluorobenzaldehyde was stirred and heated under reflux for 4 hours, using a Dean-Stark trap to remove by-product water from the distillate. The hot reaction mixture was filtered to remove some residual solid. The filtrate was set aside and allowed to stand at room temperature for 19 days. The solid formed was collected by filtration and washed with a minimal amount of ether to yield 2.24 g of the desired product as a dark blue solid, mp 219°–224° C.

EXAMPLE 2

1,4-Dihydroxy-5,8-bis[[2-[(phenylmethylene)amino]ethyl]amino]-9,10-anthracenedione A suspension of 2.00 g (0.0057 mole) of the free base, 1,4-bis[(2-aminoethyl)amino]-5,8-dihydroxyanthraquinone (prepared as described in Example 1) in 60 ml of toluene containing 1.82 g (0.0171 mole) of benzaldehyde was stirred and heated under reflux for 4 hours, using a Dean-Stark trap to remove by-product water. The hot reaction mixture was filtered to remove some residual solid which was washed with a minimal amount of toluene. The combined filtrate and wash was allowed to stand at room temperature for 13 days. The solid formed was collected by filtration and washed with a minimum of ether to yield 1.80 g of the product of the Example as a dark blue solid, mp 174°–179° C.

EXAMPLES 3–20

Additional Schiff Bases of [(aminoalkyl or substituted aminoalkyl)amino]-9,10-anthracenediones listed in Table III have been prepared by the following general procedure: A suspension of 2.0 g (0.0057 mole) of 1,4-bis[(2-aminoethyl)amino]-5,8-dihydroxyanthraquinone (free base prepared as described in Example 1) in 55–60 ml of benzene, containing 0.0171 mole of the desired aliphatic or aromatic aldehyde was stirred and heated under reflux for 4–5 hours, using a Dean-Stark trap to remove by-product water. The reaction mixture was filtered while hot to remove residual solid and the filtrate was allowed to stand at room temperature from 1–24 days. The crystallized products were collected by filtration and washed with a minimum of ether.

TABLE III

Schiff Bases of Certain Bis[(aminoalkyl)amino]-dihydroxy-9,10-anthracenediones

| Ex. | Aldehyde | Weight In Grams | Reflux Time In Hours | Product | R₂ | Yield In Grams | MP °C. |
|---|---|---|---|---|---|---|---|
| 3 | Naphthaldehyde | 2.67 | 4 | 1,4-Dihydroxy-5,8-bis-[[2-[(1-naphthalenylmethylene)amino]ethyl]amino]-9,10-anthracenedione | 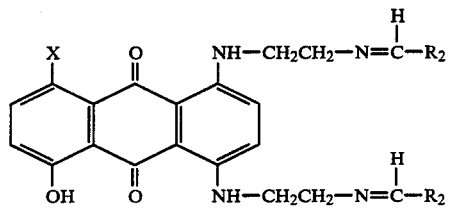 | 2.22 | 100–103 |

TABLE III-continued

Schiff Bases of Certain Bis[(aminoalkyl)amino]-dihydroxy-9,10-anthracenediones

| Ex. | Aldehyde | Weight In Grams | Reflux Time In Hours | Product | R₂ | Yield In Grams | MP °C. |
|---|---|---|---|---|---|---|---|
| 4 | 2,4-Dimethoxy-benzaldehyde | 2.84 | 4 | 1,4-Bis[[2-[[(2,4-dimethoxyphenyl)-methylene]amino]ethyl]-amino]-5,8-dihydroxy-9,10-anthracenedione | 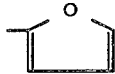 | 1.08 | 110–115 |
| 5 | 2-Furaldehyde | 1.72 | 4 | 1,4-Bis[[2-[(2-furanylmethylene)amino]-ethyl]amino]-5,8-dihydroxy-9,10-anthracenedione |  | 1.28 | 140–145 |
| 6 | p-Fluorobenz-aldehyde | 2.12 | 4 | 1,4-Bis[[2-[[(4-fluorophenyl)methylene]amino]ethyl]-amino]5,8-dihydroxy-9,10-anthracenedione | 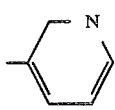 | 1.14 | 180–185 |
| 7 | 3-Pyridine-carboxaldehyde | 1.83 | 4 | 1,4-Dihydroxy-5,8-bis[[2-[(3-pyridinyl-methylene)amino]-ethyl]amino]-9,10-anthracenedione |  | 1.13 | 115–120 |
| 8 | m-Tolualdehyde | 2.06 | 4 | 1,4-Dihydroxy-5,8-bis-[[2-[[(3-methylphenyl)methylene]amino]ethyl]amino]-9,10-anthracenedione | 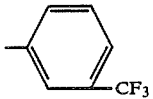 | 1.46 | 101–106 |
| 9 | α,α,α-tri-fluoro-m-tolu-aldehyde | 2.98 | 4 | 1,4-Dihydroxy-5,8-bis-[[2-[[[3-(trifluoromethyl)phenyl]methylene]amino]ethyl]-amino]-9,10-anthracenedione | 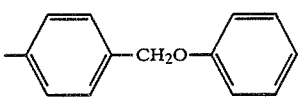 | 1.30 | 180–184 |
| 10 | 4-Benzyloxy-benzaldehyde | 3.63 | 4 | 1,4-Dihydroxy-5,8-bis-[[2-[[[4-(phenylmethoxy)phenyl]methylene]-amino]ethyl]amino]-9,10-anthracenedione | 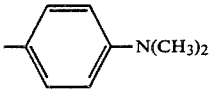 | 1.57 | 140–145 |
| 11 | p-Dimethyl-aminobenzal-dehyde | 2.55 | 4 | 1,4-Bis[[2-[[[4-(dimethylamino)phenyl]-methylene]amino]-ethyl]amino]-5,8-dihydroxy-9,10-anthracenedione | 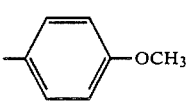 | 0.81 | 96–101 |
| 12 | p-Anisaldehyde | 2.32 | 5 | 1,4-Dihydroxy-5,8-bis-[[2-[[(4-methoxyphenyl)methylene]amino]-ethyl]amino]-9,10-anthracenedione | 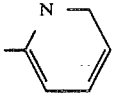 | 2.95 | 187–190 |
| 13 | 2-Pyridinecar-boxaldehyde | 1.83 | 5 | 1,4-Dihydroxy-5,8-bis-[[2-[(2-pyridinyl-methylene)amino]ethyl]amino]-9,10-anthracenedione | | 1.93 | 148–152 |

TABLE III-continued

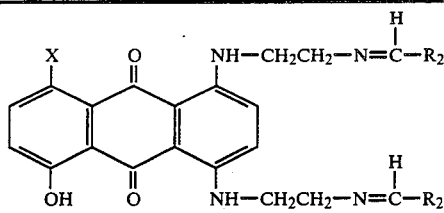

Schiff Bases of Certain Bis[(aminoalkyl)amino]-dihydroxy-9,10-anthracenediones

| Ex. | Aldehyde | Weight In Grams | Reflux Time In Hours | Product | R₂ | Yield In Grams | MP °C. |
|---|---|---|---|---|---|---|---|
| 14 | 4-Cyanobenz- aldehyde | 2.24 | 5 | 4,4'-[(9,10-Dihydro- 5,8-dihydroxy-9,10- dioxo-1,4-anthracene- diyl)bis(imino-2,1- ethanediylnitrilo- methylidyne]bisbenzo- nitrile | ―⟨C₆H₄⟩―CN | 1.84 | 234–239 |
| 15 | 3,5-Dimethoxy- benzaldehyde | 2.84 | 5 | 1,4-Bis[[2-[[(3,5- dimethoxyphenyl)- methylene]amino]- ethyl]amino]-5,8-di- hydroxy-9,10-anthra- cenedione | ―⟨C₆H₃⟩(OCH₃)(OCH₃) | 3.19 | 165–170 |
| 16 | 2-Bromobenz- aldehyde | 3.16 | 4 | 1,4-Bis[[2-[[(2- bromophenyl)methyl- ene]amino]ethyl]- amino]5,8-dihydroxy- 9,10-anthracenedione | ―⟨C₆H₄⟩―Br | 3.35 | 193–198 |
| 17 | 2-Hydroxy-4- methoxybenz- aldehyde | 2.60 | 5 | 1,4-Dihydroxy-5,8-bis- [[2-[[(2-hydroxy-4- methoxyphenyl)methyl- ene]amino]ethyl]- amino]-9,10-anthra- cenedione | ―⟨C₆H₃⟩(OH)(OCH₃) | 1.02 | 215–220 |
| 18 | 2-Thiophene- carboxaldehyde | 1.92 | 5 | 1,4-Dihydroxy-5,8-bis- [[2-[(2-thienylmeth- ylene)amino]ethyl]- amino]-9,10-anthra- cenedione | ―⟨thienyl, S⟩ | 1.94 | 168–174 |
| 19 | 4-Pyridine- carboxaldehyde | 1.83 | 5 | 1,4-Dihydroxy-5,8-bis- [[2-[(4-pyridinyl- methylene)amino]- ethyl]amino]-9,10- anthracenedione | ―⟨pyridinyl, N⟩ | 1.00 | 189–194 |
| 20 | Acetaldehyde | 0.75 | 5 | 1,4-Bis[[2-(ethyli- deneamino)ethyl]- amino]-5,8-dihydroxy- 9,10-anthracenedione | CH₃ | 0.62 | 115–120 |

Additional aldehyde-derived compounds which have been made by following the general procedure for Examples 3–20 are:
1,4-Dihydroxy-5,8-bis[[2-[(1-H-pyrrol-2-ylmethylene)amino]ethyl]amino]-9,10-anthracenedione;
1,4-Dihydroxy-5,8-bis[[2-(methyleneamino)ethyl]amino]-9,10-anthracenedione;
1,4-Bis[[2-(butylideneamino)ethyl]amino]-5,8-dihydroxy-9,10-anthracenedione;
1,4-Bis[[2-(heptylideneamino)ethyl]amino]-5,8-dihydroxy-9,10-anthracenedione.

When acetone and cyclohexanone were substituted for the aldehyde precursor in the general procedure for Examples 3–20 and the solvent was benzene or toluene the following compounds were obtained: 1,4-Dihydroxy-5,8-bis[[2-[(1-methylethylidene)amino]ethyl]amino]-9,10-anthracenedione;
1,4-Bis[[2-(cyclohexylideneamino)ethyl]amino]-5,8-dihydroxy-9,10-anthracenedione.

EXAMPLE 21

1,4-Dihydroxy-5,8-bis[[3-[(phenylmethylene)amino]propyl]amino]-9,10-anthracenedione A suspension of 0.0057 mole of 1,4-bis[(3-aminopropyl)amino]-5,8-dihydroxyanthraquinone [prepared by the method of C. W. Greenhalgh and N. Hughes, J. Chem. Soc. (C), 1284 (1968)] in 60 ml of benzene containing 0.0171 mole of benzaldehyde is refluxed and treated as described in the general procedure for Examples 3–20 to give the title compound.

EXAMPLE 22

2,3-Dihydro-5,8-dihydroxy-1,4-bis[[2-[(1-naphthalenyl-methylene)amino]ethyl]amino]-9,10-anthracenedione A suspension of 0.0057 mole of the free base, leuco-1,4-bis(2-aminoethylamino)-5,8-dhydroxyanthraquinone (prepared as described in Example 12 of U.S. Pat. No. 4,197,249) in 60 ml of benzene containing 0.0171 mole of naphthaledehyde is refluxed and treated as described in the general procedure for Example 3-20, to yield the desired product.

EXAMPLE 23

1,4-Bis[[3-[[(4-fluorophenyl)methylene]amino]propyl]amino]-2,-dihydro-5,8-dihydroxy-9,10-anthracenedione A suspension of 0.0057 mole of the free base, leuco-1,4-bis(3-aminopropylamino)-5,8-dihydroxyanthraquinone (prepared as decribed in Example 13 of U.S. Pat. No. 4,197,249) in 60 ml of benzene containing 0.0171 mole of p-fluorobenzaldehyde is refluxed and treated as described in the general procedure for Examples 3-20, to give the title compound.

EXAMPLE 24

1-[(2-Aminoethyl)amino]-5,8-dihydroxy-4-[[2-[(phenyl-methylene)amino]ethyl]amino]-9,10-anthracenedione A suspension of 0.0057 mole of the free base, 1,4-bis[(2-aminoethyl)amino]-5,8-dihydroxyanthraquinone (prepared as described in Example 1) in 60 ml of benzene containing 0.0057 mole of benzaldehyde is refluxed and treated as described in the general procedure for Examples 3-20, to give the desired product.

EXAMPLE 25

1,4-Bis[[2-[(2-pyridinylmethylene)amino]ethyl]amino]-9,10-anthracenedione

A suspension of 0.0057 mole of the free base, 1,4-bis[(2-aminoethyl)amino]anthraquinone [prepared by the method of C. W. Greenhalgh and N. Hughes, J. Chem. Soc. (C) 1284 (1968)] in 60 ml of benzene containing 0.0171 mole of 2-pyridinecarboxaldehyde is refluxed and treated as described in the general procedure for Examples 3-20 to yield the product of the Example.

EXAMPLE 26

Preparation of Parenteral Suspension

In a solution of 700 ml of propylene glycol and 200 ml of water for injection is suspended 20.0 g of 1,4-dihydroxy-5,8-bis[[2-[(phenylmethylene)amino]ethyl]amino]-9,10-anthracenedione with stirring. After suspension is complete, the volume is made up to 1000 ml with water for injection. The formulation is sterilized, filled into 5.0 ml ampoules, each containing 2.0 ml (representing 40 mg of drug) and sealed under nitrogen.

EXAMPLE 27

Preparation of Parenteral Suspension

The active compound in powder form is sterilized by ethylene oxide sterilization. The sterilized powder is aseptically filled into vials in dosage unit form and the vials are sealed. Immediately prior to use the powder is suspended by the addition of a suitable sterile diluent. The resulting suspension may be sonicated if necessary to promote dispersion. (This mode of suspension is advantageous for compounds which might undergo some hyrolysis on long standing in an aqueous medium.)

I claim:

1. A compound of the formula:

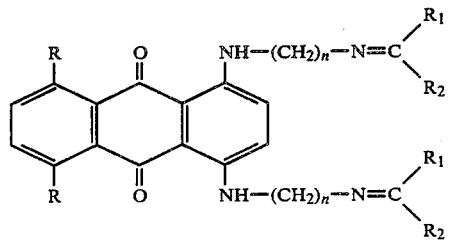

wherein n is 2 or 3; R is hydrogen or hydroxy; $R_1$ is hydrogen or alkyl($C_1$-$C_3$); $R_2$ is hydrogen, alkyl($C_1$-$C_6$), 1-naphthyl, 2-naphthyl, 2-furyl, 3-furyl, 2-thienyl, 3-thienyl, 2-pyridyl, 3-pyridyl, 4-pyridyl, pentafluorophenyl or a moiety of the formula:

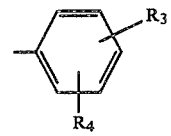

wherein $R_3$ and $R_4$ may be the same or different and are each hydrogen, hydroxy, fluoro, chloro, bromo, cyano, trifluoromethyl, alkyl($C_1$-$C_3$), alkoxy($C_1$-$C_3$), dimethylamino or benzyloxy; and $R_1$ and $R_2$ taken together is —$(CH_2)_m$— wherein m is 4, 5 or 6.

2. The compound according to claim 1; 1,4-bis[2-(pentafluorophenylmethyleneamino)ethylamino]-5,8-dihydroxy-9,10-anthracenedione.

3. The compound according to claim 1; 1,4-bis[2-(phenylmethyleneamino)ethylamino]-5,8-dihydroxy-9,10-anthracenedione.

4. The compound according to claim 1; 1,4-bis[2-(1-naphthylmethyleneamino)ethylamino]-5,8-dihydroxy-9,10-anthracenedione.

5. The compound according to claim 1; 1,4-bis[2-(2,4-dimethoxyphenylmethyleneamino)ethylamino]-5,-8-dihydroxy-9,10-anthracenedione.

6. The compound according to claim 1; 1,4-bis[2-(2-furylmethyleneamino)ethylamino]-5,8-dihydroxy-9,10-anthracenedione.

7. The compound according to claim 1; 1,4-bis[2-(4-fluorophenylmethyleneamino)ethylamino]-5,8-dihydroxy-9,10-anthracenedione.

8. The compound according to claim 1; 1,4-bis[2-(3-pyridylmethyleneamino)ethylamino]-5,8-dihydroxy-9,10-anthracenedione.

9. The compound according to claim 1; 1,4-bis[2-(3-methylphenylmethyleneamino)ethylamino]-5,8-dihydroxy-9,10-anthracenedione.

10. The compound according to claim 1; 1,4-bis[2-(3-trifluoromethylphenylmethylenamino)ethylamino]-5,8-dihydroxy-9,10-anthracenedione.

11. The compound according to claim 1; 1,4-bis[2-(4-benzyloxyphenylmethyleneamino)ethylamino]-5,8-dihydroxy-9,10-anthracenedione.

12. The compound according to claim 1; 1,4-bis[2-(4-dimethyaminophenylmethyleneamino)ethylamino]-5,8-dihydroxy-9,10-anthracenedione.

13. The compound according to claim 1, 1,4-bis[2-(4-methoxyphenylmethyleneamino)ethylamino]-5,8-dihydroxy-9,10-anthracenedione.

14. The compound according to claim 1, 1,4-bis[2-(2-pyridylmethyleneamino)ethylamino]-5,8-dihydroxy-9,10-anthracenedione.

15. The compound according to claim 1, 1,4-bis[2(4-cyanophenylmethyleneamino)ethylamino]-5,8-dihydroxy-9,10-anthracenedione.

16. The compound according to claim 1, 1,4-bis[2(3,5-dimethoxyphenylmethyleneamino)ethylamino]-5,8-dihydroxy-9,10-anthracenedione.

* * * * *